United States Patent [19]
Barnes et al.

[11] Patent Number: 4,761,326
[45] Date of Patent: Aug. 2, 1988

[54] FOAM COATED CSR/SURGICAL INSTRUMENT WRAP FABRIC

[75] Inventors: Charles G. Barnes; A. Frank Baldwin, both of Greensboro, N.C.

[73] Assignee: Precision Fabrics Group, Inc., Greensboro, N.C.

[21] Appl. No.: 59,949

[22] Filed: Jun. 9, 1987

[51] Int. Cl.⁴ .................. B32B 27/04; B32B 5/20; B32B 5/32

[52] U.S. Cl. .................. 428/219; 428/286; 428/288; 428/290; 428/296; 428/304.4; 428/306.6; 428/311.1; 428/311.5; 428/315.5; 428/315.9; 428/316.6

[58] Field of Search .............. 428/219, 220, 286, 288, 428/290, 296, 304.4, 306.6, 308.4, 310.5, 311.1, 311.5, 311.7, 315.5, 315.7, 315.9, 316.6, 317.5, 317.9

[56] References Cited

U.S. PATENT DOCUMENTS

| | | | |
|---|---|---|---|
| 3,527,654 | 9/1970 | Jones et al. | 428/159 |
| 3,567,565 | 3/1971 | Jones et al. | 428/309.1 |
| 3,615,970 | 10/1971 | May | 156/78 |
| 3,642,563 | 2/1972 | Davis et al. | 428/220 |
| 3,748,217 | 7/1973 | May et al. | 428/286 |
| 3,862,291 | 1/1975 | Brandon, Jr. et al. | 264/321 |
| 4,016,831 | 4/1977 | James et al. | 118/415 |
| 4,072,775 | 2/1978 | James et al. | 427/373 |
| 4,353,945 | 10/1982 | Sampson | 428/315.9 |
| 4,362,774 | 12/1982 | Brandon, Jr. et al. | 428/159 |
| 4,387,118 | 6/1983 | Shelton | 427/176 |
| 4,439,473 | 3/1984 | Lippman | 428/219 |
| 4,499,139 | 2/1985 | Schortmann | 428/245 |
| 4,630,603 | 12/1986 | Greenway | 428/304.4 |
| 4,657,804 | 4/1987 | Mays et al. | 428/315.9 |
| 4,681,798 | 7/1987 | Gill et al. | 428/219 |

Primary Examiner—William J. Van Balen
Attorney, Agent, or Firm—Nixon & Vanderhye

[57] ABSTRACT

A sterilizable, water vapor permeable, bacterial barrier foam-coated medical fabric suitable for use as a medical instrument wrap or CSR wrap which features a nonwoven textile-type substrate coated with a continuous network of an open cell microporous foam that forms a network of interconnected cells distributed among and covering nearly the entire surface of the substrate. This foam extends into the substrate itself and presents a network of interconnected cells that form a tortuous path from the face of the fabric to the opposite side of the fabric to define a bacterial barrier to inhibit or stop the passage of bacteria, yet permits steam and water vapor to pass into and out of the fabric.

25 Claims, 1 Drawing Sheet

BLUE FOAM COATED FABRIC 150X

BLUE FOAM COATED FABRIC 150X

BLUE FOAM COATED FABRIC 500X

4,761,326

FOAM COATED CSR/SURGICAL INSTRUMENT WRAP FABRIC

BACKGROUND OF THE INVENTION

This invention relates to a fabric used to wrap surgical instruments and medical devices and appliances that are to be sterilized. The fabric has a foam coating on at least one surface that extends into the fabric substrate, the coating composed of an open-celled hydrophobic polymeric foam that allows gaseous sterilizing materials, such as steam or ethylene oxide gas, to penetrate the foam and, in turn, contact surgical instruments wrapped in the fabric while providing bacterial filtration/barrier properties. The fabric is repellent to alcohol, water, and saline and is flexible, opaque and easily sterilized using conventional hospital sterilization equipment. Optionally, the fabric may be a composite structure with two fabric plies surrounding an open-celled hydrophobic polymeric foam layer.

It is common practice in a hospital surgical supply or central supply room (often identified by its abbreviation CSR) to wrap instruments or medical devices and appliances prior to sterilization. These packages are typically wrapped with a textile or nonwoven fabric which serves to protect the instruments during sterilization and to preserve their sterility upon subsequent storage. Fabrics which are typically used in this area are either tightly woven textiles or nonwovens which possess a closed structure. Presently, there are several nonwoven fabrics available which are economically attractive, but do not possess the appropriate physical properties.

An objective of this invention is to provide a procedure that upgrades a non-uniform, low filtration efficiency fabric and imparts to it high filtration efficiency and uniformity, coupled with water/fluid repellency, sterilizability, and opacity, all within economic limits.

It has been discovered that the application of an open-celled hydrophobic polymeric stable foam compound coated onto the surface of a suitable substrate or sandwiched between two fabric plies, the foam penetrating the substrate or, if a plied structure, one of the substrates, to varying degrees. The fabric exhibits the combined effects of good permeability to steam or ethylene oxide sterilizing gases while offering adequate bacterial filtration efficiency. In addition, the product will possess adequate fluid repellency to prevent transmission of bacteria. The product is non-toxic in accordance with current industry and federal guidelines, and is substantially lint free, odor free, and drapeable.

BRIEF DESCRIPTION OF THE DRAWINGS

The invention will be further explained with reference to the attached drawings, all electron photomicrographs, of an illustrative foam coated CSR/surgical instrument wrap fabric according to the invention.

SUMMARY OF THE INVENTION

Figure 1:
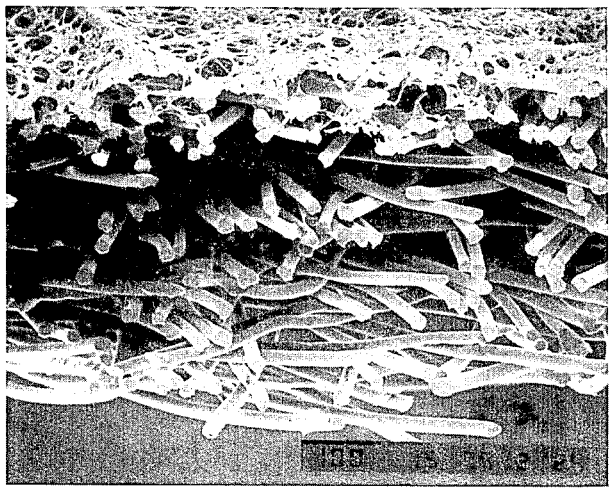
FIG. 1 is a cross-sectional view (magnification of 150×) of a foam coated nonwoven fabric showing the foam coating distributed over the top surface of the fabric.

Described is a sterilizable, water vapor permeable, bacterial barrier foam-coated medical fabric suitable for use as a medical instrument wrap or CSR wrap. The medical fabric features a nonwoven textile-type substrate coated with a continuous network of an open cell microporous foam that forms a network of interconnected cells distributed among and covering nearly the entire surface of the substrate. This foam extends into the substrate itself and presents a network of interconnected cells that form a tortuous path from the face of the fabric to the opposite side of the fabric to define a bacterial barrier to inhibit or stop the passage of bacteria, yet permits steam and water vapor to pass into and out of the fabric. In another embodiment, the fabric is a composite of two plies of nonwoven textile substrate sandwiched around an open cell microporous foam layer, as described. The medical fabric of this invention, in single or multiple form, has a Frazier air permeability at 0.5 inches water column of about 50 to about 250 cfm (INDA 70.1-70) and a bacterial filtration efficiency for a single ply of the fabric of at least 60% according to military specification 36954C. Preferably, the fabric has from about 0.2 to about 0.75 ounces of foam solids per square yard of substrate.

DETAILED DESCRIPTION OF THE INVENTION

Water vapor permeable foam-coated medical fabric useful as a medical instrument wrap or CSR wrap must satisfy several requirements. The product should not allow objectionable material to leach into the environment when exposed to steam or other commonly encountered fluids. The fabric should meet current federal and industry standards for flammability. Other requirements include adequate functional strength and durability during processing and use. The product of this invention has the above qualities and serves as a functional replacement for expensive, heavy weight fabric currently in use.

In addition, the foam coated CSR/surgical instrument wrap should not bleed color or change color on autoclaving or exposure to ethylene oxide, have good adhesion to autocalve tape, be soft and flexible before and after sterilization with no or only limited "memory", and be non-toxic within medical device guidelines.

The instrument wrap fabric of this invention is a foam-coated nonwoven in which the foam provides a barrier to bacteria. This foam barrier layer is located on one surface of the fabric and penetrates down into a substantial portion of the fabric itself. The photomicrographs forming the drawings, as discussed in more detail below, show a continuous network of an open cell foam distributed among the fibers of the fabric surface when viewed at a magnification of 100×. At 1000×, these small open cells appear to form an open network of interconnected cells when viewed from both the face and the back surface of the fabric, and appear to define an open but tortuous path from the face of the fabric to the back.

It has been determined that some nonwovens are in general unacceptable because of their open structure, while the foam coating provides the appropriate physical properties essential to permit the fabric to act as a bacterial barrier. Unlike prior proposals, notably U.S. Pat. No. 4,499,139, there is no band, zone, internal area of the substrate or strata in the web of the nonwoven material of the product of this invention; rather, the foam is distributed over the top face and penetrates down into most of the nonwoven web itself. This is achieved by forcing the foam into as much of the nonwoven web as possible. When two plies of nonwoven substrate are used (see below) the foam penetrates into both of the plies holding them together to form a secure composite structure.

Another embodiment of the medical fabric of this invention is a composite formed of two layers or plies of nonwoven textile on either side of the open cell microporous, hydrophobic foam of the type described. A multiple ply medical fabric is prepared by applying a foam layer, in the manner described in detail below, then joining an upper or top ply to the foam-coated surface, the foam extending into both plies to bond the two together.

An important requirement for an acceptable instrument wrap is the ability of the wrap to allow steam to enter and be released from a pack of instruments or other object(s) wrapped within the fabric. During sterilization procedures, steam is forced into the package in order to accomplish sterilization. It is important that the steam or water introduced into the package be easily removed during the drying cycle, so as to avoid trapping water in the package leaving the instruments wet. Thus, an acceptable instrument wrap fabric must not only present a barrier to bacteria, it must also have good steam and water transport properties.

Foam-coated and foam-backed textile materials are described in the patent literature, primarily relating to domestic textiles and upholstery fabric. As examples, see U.S. Pat. No. 3,615,970, describing a glass fabric having a foam polymer backing for a drapery, U.S. Pat. No. 3,748,217 in which a foam organic polymer bonds a textile fabric to a spunlaced nonwoven fabric, again for drapery face fabrics. See also U.S. Pat. Nos. 3,862,921, and 4,362,774 relating to foam-backed drapery fabrics. Various techniques of applying foam to textile substrates are also described in the patent literature, as evidenced by U.S. Pat. Nos. 3,862,291, 4,362,774 and 4,387,118. Other foam polymer applications and procedures are described in U.S. Pat. Nos. 3,527,654, 3,567,565 and 3,642,563.

Figure 2:
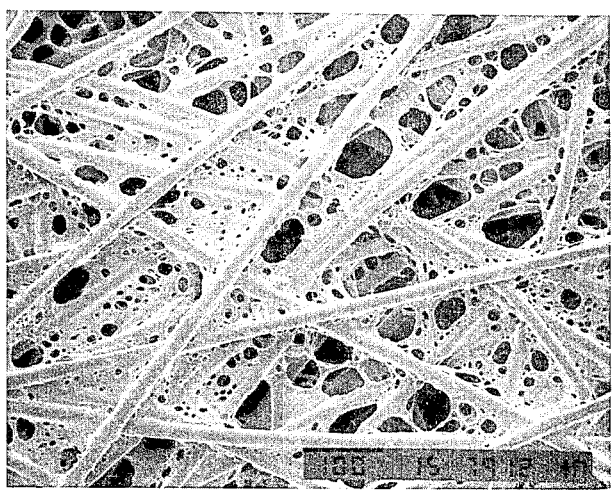
FIG. 2 is a top view of the same foam coated fabric also at a magnification of 150× showing the foam coating between the adjoining fibers of the nonwoven substrate forming a network of pores of various sizes along the top layer of the fabric.
Figure 3:
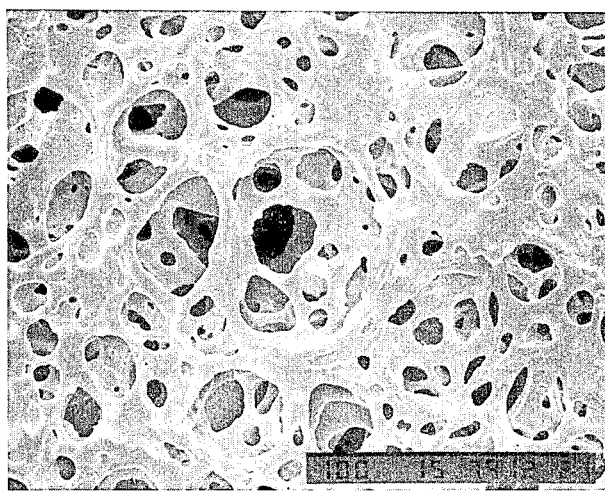
FIG. 3 is an enlarged view at 500× magnification of the top view as in FIG. 2 showing in more detail the network of interconnected pores that form the bacterial barrier on the top surface of the fabric.

U.S. Pat. No. 4,499,139 describes forming a strata or layer within the single ply fibrous web, as depicted in FIGS. 1 and 2 of this patent in which the froth is worked into the fabric to form interconnecting links to hold the surface fibers in place. The face of the fabric is scraped free of froth so that the outermost fibers on both the top and bottom surfaces are substantially froth-free. The instrument wrap fabric of the present invention has an entirely different structure with a quantity of foam on at least one surface of the fabric as well as the foam penetrating most, if not all, of the nonwoven fabric web.

Performance properties and characteristics of the instrument wrap fabrics may be conveniently varied by adjusting the weight of solids applied to the nonwoven substrate and, more importantly, selecting an appropriate basis weight of the nonwoven substrate or by using a second ply of nonwoven substrate adhered to the opposite side of the foam layer. As examples, increasing the basis weight of the nonwoven textile will result in different types or grades of product. Basis weights for the nonwoven textile fall with a range of about 0.7 to 3.0 g usually 0.09 to 1.5, ounces per square yard and each ply of double ply products having a basis weight ranging from 0.7 to 1.25 ounces per square yard. Suitable nonwoven textiles include hydroentangled nonwovens, point bonded polyolefin spunbonded nonwovens, thermal bonded polyester nonwovens, and polyolefin nonwovens. Polypropylene is the preferred polyolefin fiber.

The foam coated CSR/surgical instrument wrap fabrics of the present invention are prepared as follows: a stable, open-celled, hydrophobic polymeric foam is created by the mechanical induction of air into a suitable aqueous coating compound. A typical composition for a material of this type is as follows:

| Ingredient | Wet-part |
| --- | --- |
| aqueous emulsion polymer dispersion (40-50% solids) | 200 |
| clay, talc or other filler | 10-20 |
| surfactant: foaming aid | 2-6 |
| synthetic thickeners | 1-5 |
| water repellent | 10-20 |
| ammonium stearate (30%) | 8-20 |
| aqua ammonia (28%) | 1-5 |

Foams based upon this formulation are prepared and applied to textile substrates according to known techniques.

Formulations falling within the above known recipe are aerated in a mechanical foamer, such as an Oakes foamer, or Texilease foamer. For laboratory purposes a Hobart, Kitchen-Aid or hand mixer may be used to prepare foams. The formulation is aerated to produce foams which are from five parts air: one part formula to twenty parts air: one part formula. Application of the resulting foam to the substrate is accomplished by either a surface technique, such as applying a bank of aerated compound to the substrate, or by dipping the substrate through the aerated compound.

The thus applied foam is then coated onto and at least partially pressed into the textile substrate by various techniques. Examples of suitable techniques include knife over roll coating, knife over table coating, knife over gap, knife over blanket, floating knife, air knife, and gapped pad.

The foam may be applied to either one side or both sides of the substrate. The coated fabric is then oven dried and cured. Drying time and cure temperatures are well known to those skilled in the art. The cured, coated fabric may then be crushed or calendared as required by the end use.

The invention is further described with respect to the following examples in which all parts of percentages are expressed on the basis of weight and temperatures reported in ° F. unless indicated otherwise.

EXAMPLE I

A spunbonded, point embossed 0.9-1.5 oz/sq. yd. polypropylene nonwoven fabric was used as the substrate. The uncoated fabric had a semi-transparent appearance. It was selected to be as free of residual finish, antistatic, lubricants, short chain polymer, etc., as possible, and to present a relatively smooth, uniform surface for coating later. It has been found that the properties of the product will be improved if the fiber distribution is even and the denier variation of the fiber is minimized.

While a specific fabric was chosen for this example, a wide range of both synthetic and natural fibers are suitable for this use as well as a variety of fabric formations.

A coating compound was prepared on the basis of the following formulation:

| Filler/color dispersion | | |
|---|---|---|
| Component Parts | Wet Parts | Dry |
| water | 87.0 | 0.0 |
| tetra sodium pyrophosphate | 1.0 | 1.0 |
| Tamol 731 (25%) | 1.6 | .4 |
| Kaoplate (clay) | 70.0 | 70.0 |
| TiO$_2$ | 30.0 | 30.0 |
| phthalo-cyanine blue (30%) | 4.0 | 1.2 |
| | 193.6 | 102.6 (53.0%) |

| Coating Compound | | |
|---|---|---|
| Component | Wet Parts | Dry Parts |
| hydrophobic acrylic latex (Hycar 2600 × 334, R & H E-940) | 300 | 135.0 |
| filler/color dispersion (above) | 116 | 61.5 |
| malamine cross link resin | 10 | 8 |
| or | | |
| epoxy cross link resin (Celanese 55-5003) | (60) | (30) |
| foaming aid-surfactant | 3 | 1.0 |
| anionic or non-ionic repellent fluor-chemical (Zonyl NWA, Milease F-14) | 15 | 3.5 |
| wax dispersion (optional) | 20 | 5.0 |
| catalyst | 3 | 3.0 |
| ammonia (28%) | to pH 7.5–9.5 | |
| ammonium stearate dispersion | 20 | 6.0 |
| | 487.0 | 223.0 (45.8%) |

Alternate mineral fillers suitable for the filler/color dispersion include kaolin clay, talc, feldspar, pyrophyllite, alumina and calcium carbonate. Titanium dioxide is optional; when present it serves as an opacifier and imparts a more attractive look to a semi-transparent substrate. An appropriate colored pigment may be included, as desired.

The foam coating is prepared first by mixing the solid fillers and colors to form a dispersion. A filler or mixture of several fillers is necessary to occupy the fiber interstices and fill the otherwise void spaces between adjacent fibers to provide the necessary bacterial filtration. Suitable fillers are inorganic mineral fillers such as clays, talcs and carbonates, all as listed above. An opacifier or white pigment such as titanium dioxide may be included, if desired, to lend the correct degree of opacity, or it may be omitted entirely, as explained above. These solid, substantially insoluble particles are dispersed in water with the use of a dispersing aid or surfactant.

The coating composition is based upon a resin or combination of resins plus filler(s) and indeed the filler(s) may represent fully half of the total weight of the two components. Other necessary ingredients include a foaming aid or surfactant to assist in forming a stable foam plus any other reactants or auxiliaries required to cross-link the resin and form a foam that, upon drying, remains stable and continues to exhibit the desired performance characteristics over the life of the article. Usually a CSR/surgical instrument wrap is intended for a single use, then discarded.

The polymer employed may be an acrylic, styrene-butadiene rubber (SBR), vinyl acetate, urethane, vinyl chloride or vinylidene chloride polymer, preferably in the form of a dispersion, and in a polymer to filler weight ratio of 50:50 to 100:0 with the preferred ratio of about 70:30. Total solids of the coating composition range from 40 to 70% by weight. The pH of the composition may be adjusted by the addition of a suitable base, such as ammonia, to maintain a pH in the range of 7 to 10, preferably in the range of pH 8 to 9. The coating composition, prior to foaming, should have a viscosity of from about 400 to 2,000 cps with a viscosity of about 600 to 900 cps preferred. A thickener may be included to achieve the best viscosity. The coating composition is usually maintained and applied at a temperature in the range of from 70° F. to 110° F.

The fluorocarbon repellent component is typically a dispersion of fluoropolymer in water. See generally Fluorine-Containing Polymers, Encyclopedia of polymer Science & Technology, pp. 179–203, Interscience, 1967, the disclosure of which is hereby incorporated by reference. The fluoropolymer component may be selected from a host of commercially available products including DuPont's Zonyl NWG, Zonyl NWF, Zepel RS, Zepel RN and 3-M's FC-831, FC-834 and FC-461. It is the fluorocarbon component that provides alcohol repellency to the finished fabric; the requisite amount of fluorocarbon component needed to achieve the alcohol repellency desired (see the relevant test, below) is used. One will select a repellent fluorocarbon component that is compatible with the system, i.e., the other bath components and processing conditions, is economical and provides the required alcohol repellency. As the fluorocarbon component is more expensive than the wax/resin extender, described below, it is desirable to use the smallest amount of the more expensive component as possible.

The coating composition is mechanically foamed in a foam generator such as an Oakes foamer or a L.E.S.S. model 500 super foamer to achieve a ratio of from five to eleven parts air to one part coating composition, with a ratio of 6:1–8:1 being preferred.

The compound is then applied by any convenient means, such as screen, roller, gravure and preferably, a knife coater. The coater is adjusted to apply the coating to the fabric in a fashion so as to both impregnate and surface coat the material. A knife over gap arrangement having a rounded or beveled knife set over a two inch gap with the blade being set at -0.055" below the plane of the fabric is used. The fabric is then run through the coater at a speed of from 50 to 80 yards per minute. The combination of pressure and scraping action forces the coating into the fabric while leaving a thin surface coat.

Based upon the above formulation, a coating weight of between 0.2–0.75 oz/sq. yd. of solids should be applied with 0.3–0.4 oz. being a desirable weight.

The fabric is then dried at 220°–285° F. in a conventional hot air tenter frame or dryer at a speed which allows for at least eighteen seconds of drying time. The coating may be crushed between a set of rollers which are typically rubber over steel or steel over steel. Following the optional step of crushing, the fabric is post cured for an additional thirty seconds to two minutes at 285° F. During the post cure, an additional finish may be applied to enhance the fabric properties, improve repellency, add softness and reduce blocking. The post cure may be omitted if all properties ae achieved in the coating pass. The finished fabric is then trimmed and packaged.

The resulting fabric should exhibit the following properties:

| Property | Method | Values |
|---|---|---|
| basis wt. oz/sq. yd | INDA 130.0 - 70 | 0.7–3.0 |
| strength | ASTM D 1117-77 (grab tensile) | 22# MD 13# XD |
| burst strength | INDA 30 - 70 | 20 psi |
| Frazier air permeability @0.5" W.C. | INDA 70.1 - 70 | 50–250 cfmm |
| saline repellency | INDA 80.7 - 7-0 | 15 minutes |
| spray rating | AATCC 22 - 1980 | 70–100 |
| alcohol | INDA 80.9 - 74 | 7 repellency |
| resistance to linting | INDA 160.0 - 83 Modified Gelbo-flex | 600 counts @ 1 micron |
| bacterial filtration | Mil spec. 36954C 4.4.1.1.1. protocol ARO/007 *Staph. aureus* | 1 ply 60% min. 2 ply 70% min. |
| flammability | C.S. 191-53 NFPA - 702 | Class I Class I or II |

Basis weight, strength and burst strength—are measured according to the procedures indicated. These values depend in large part on the nature of the substrate itself.

Frazier air permeability—is a measure of the foam-coated fabric's ability to transmit air and is measured according to International Nonwovens and Disposables Association (INDA) test 70.1-70.

Saline repellency—is measured according to INDA test IST 80.7-70 (R77), sometimes referred to as the mason jar test. In this test, a swatch of sample fabric is placed over the mouth of a mason jar containing sufficient normal saline (0.9% NaCl) that when the jar is inverted a 4.5" head of water results. The top ring is screwed onto the jar, the jar is inverted and placed on a glass plate. The inverted jar is observed and the time is measured until the jar leaks. The minimum time for a successful sample is 15 minutes for an instrument wrap fabric.

Spray rating, a measure of water repellency—the subject fabric should have a minimum value of 70 according to the American Association of Textile Chemists and Colorists (AATCC) spray rating test 22—1980. In this test, the fabric is held tightly on a metal hoop and sprayed with 25 ml. of water. The fabric is then rated by comparison of the sprayed fabric with pictures on a standard chart.

Alcohol repellency—is measured in a test in the manner of INDA test IST 80.9-74 (R77) which uses ethanol. This test was modified in that isopropanol was the alcohol that was used. In this test equal amounts of serially diluted isopropanol solutions, ranging from 60% to 100% in increments of 10 percent, are placed on a sample fabric arranged on a flat surface such as a laboratory counter top. After five minutes, the surface is usually inspected and the highest concentration retained by the sample fabric is noted. The minimum value is a 70% isopropanol solution, i.e., a 70% isopropanol solution is retained by the fabric but the 80% solution penetrates through the fabric to the underlying surface. Fabric according to my invention typically retains 80% and 90% isopropanol solutions.

Resistance to linting—is measured by INDA test IST 160.0-83 by determining the relative number of particles released from a fabric sample when subjected to continuous twisting flexure. The test is used to assess the initial cleanliness and lint generating potential of fabrics and fabric composites. Our tests used a modified Gelbo Flex Unit (Gelbo Flex Tester, Mode 5000, United States Testing Co., Hoboken, N.J.) and measured the number of particles having a minimum particle size of 1.0 micron for a period of 60 seconds at an air flow rate of 15.0 cubic feet per hour as in test method 160.1. A ten-minute total count is reported.

Bacterial filtration—was measured according to MIL Spec. 36954C, 4.4.1.1.1. Results are expressed as bacterial filtration efficiency (BFE) in terms of percent according to the following procedure:

A 24 hour culture of *Staphylococcus aureus* was diluted to a precise concentration. The culture suspension was pumped through a Chicago nebulizer at a controlled flowrate and fixed air pressure. The constant challenge delivery at a fixed air pressure formed aerosol droplets of defined size. The droplets were collected in a glass aerosol chamber and drawn through a six stage, viable particle, Andersen sampler. The flowrate for this study was 28.3 liters per minute, (LPM) or one cubic foot per minute.

The Andersen sampler, a sieve sample, impinges the aerosol droplets onto one of the six agar plates based on size. The media used was soybean case in digest agar (1.5%). The agar plates were incubated at 37° C. for 24–48 hours and the colonies formed by each bacteria laden droplet counted. Colony counts from the Andersen sampler plates were converted to probable hit values using the chart of Andersen.

The test samples were challenged by placing them between the aerosol chamber and the Andersen sampler. The filtration efficiency was calculated as a percent difference between test sample runs and runs without a test sample in place.

$$BFE \% = \frac{\text{Colonies without filter} - \text{Colonies with Filter}}{\text{Colonies without filter (Control)}} \times 100$$

This procedure produces a more severe challenge to most filtration devices than is experienced in use. The purpose with this procedure is to consistently measure, as accurately as possible, the differences between material, or difference in the same material over time.

Flammability—medical fabrics must meet the requirements of CS-191-53.

Fastness—although not required for certain end uses, if a dye or tint is included it must stay in the foam dispersion on the fabric and remain fixed, free from crocking and bleeding.

What is claimed:

1. A sterilizable, water vapor permeable, bacterial barrier foam-coated medical fabric suitable for use as a medical instrument wrap composed of a nonwoven textile substrate having a continuous network of an open cell microporous, hydrophobic foam distributed among and covering substantially the entire top surface of the textile substrate and extending into the textile substrate, the network of interconnected cells forming a tortuous path from the face of the fabric to the back of the fabric and defining a bacterial barrier yet allowing steam and water vapor to pass into and out of the fabric, the fabric having a Frazier air permeability at 0.5" W.C. (INDA 70.1–70) in the range of about 50 to about 250 cfm and a bacterial filtration efficiency (mil. spec. 36954C) for a single ply of at least 60%.

2. The sterilizable medical fabric of claim 1, in which the foam contains a polymeric binder selected from the group consisting of acrylic, styrene-butadine rubber, vinyl acetate, urethane, vinyl chloride and vinylidene chloride polymers, together with at least one filler or opacifying agent and a water repellent.

3. The sterilizable medical fabric of claim 2, having a spray rating (AATCC 22-1980) of between about 70 and 100 and a saline repellency (INDA 80.7-7.0) of at least 15 minutes.

4. The sterilizable medical fabric of claim 1, having an alcohol repellency rating (INDA 80.9-74) of at least 7.

5. The sterilizable medical fabric of claim 3, in which the polymeric binder is an acrylic resin and the foam contains titanium dioxide as an opacifier.

6. The medical fabric of claim 1, in which the textile substrate is a hydroentangled nonwoven.

7. The medical fabric of claim 1, in which the substrate is a point bonded polyolefin spunbonded nonwoven.

8. The medical fabric of claim 1 in which the substrate is a thermal bonded polyester.

9. The medical fabric of claim 1 in which the substrate is a polypropylene nonwoven.

10. The medical fabric of claim 1, in which the foam extends at least into the top 60% of the thickness of the substrate.

11. The medical fabric of claim 1, in which the fabric contains from about 0.2 to about 0.75 ounces of foam solids per square yard of substrate and an overall basis weight (INDA 130.0–70) in the range of about 0.7 to about 3.0 ounces per square yard.

12. The medical fabric of claim 11, in which the fabric contains from about 0.3 to about 0.4 ounces of foam solids per square yard of substrate.

13. A two ply, sterilizable, water vapor permeable, bacterial barrier foam-coated medical fabric suitable for use as a medical instrument wrap composed of a pair of nonwoven textile substrates having between them a continuous network of an open cell microporous, hydrophobic foam distributed among and covering substantially the entire contacting surface of each of the textile substrates and extending into each of the textile substrates, the network of interconnected cells forming a tortuous path from the face of one of the fabrics to the back of the other fabric and defining a barrier to bacterial while allowing steam and water vapor to pass into and out of the fabric, the fabric having a Frazier air permeability at 0.5" W.C. (INDA 70.1–70) in the range of about 15 to about 200 and a bacterial filtration efficiency (mil. spec. 36954C) of at least 60%.

14. The two ply, sterilizable medical fabric of claim 13, in which the foam contains a polymeric binder selected from the group consisting of acrylic, styrene-butadine rubber, vinyl acetate, urethane, vinyl chloride and vinylidene chloride polymers, together with at least one filler or opacifying agent and a water repellent.

15. The two ply, sterilizable medical fabric of claim 14, having a spray rating (AATCC 22-1980) of between about 70 and 100 and a saline repellency (INDA 80.7-7.0) of at least 15 minutes.

16. The two ply, sterilizable medical fabric of claim 13, having an alcohol repellency rating (INDA 80.9-74) of at least 7.

17. The two ply, sterilizable medical fabric of claim 3, in which the polymeric binder is an acrylic resin and the foam contains titanium dioxide as an opacifier.

18. The two ply, sterilizable medical fabric of claim 13, in which each ply has a basis weight of from about 0.7 to about 1.25 ounces per square yard.

19. The two ply medical fabric of claim 18, in which both plies of the textile substrate are hydroentangled nonwoven.

20. The two ply medical fabric of claim 18, in which both plies of the substrate are point bonded polyolefin spunbonded nonwoven.

21. The two ply medical fabric of claim 18 in which both plies of the substrate are thermal bonded polyester.

22. The two ply medical fabric of claim 18 in which both plies of the substrate are polyolefin nonwoven.

23. The two ply medical fabric of claim 13, in which the foam extends up to 60% of the thickness of each ply of the substrate.

24. The two ply medical fabric of claim 13, in which the fabric contains from about 0.2 to about 1.5 ounces of foam solids per square yard of substrate and an overall basis weight (INDA 130.0-70) in the range of about 0.7 to about 3.5 ounces per square yard.

25. The two ply medical fabric of claim 24, in which the fabric contains from about 0.3 to about 0.4 ounces of foam solids per square yard of substrate.

* * * * *